United States Patent
Pan et al.

(10) Patent No.: US 8,124,409 B2
(45) Date of Patent: Feb. 28, 2012

(54) UTILIZING LIVER CELL LINE QSG-7701 TO BE INFECTED WITH HEPATITIS B VIRUS

(75) Inventors: Xiaoben Pan, Beijing (CN); Lai Wei, Beijing (CN)

(73) Assignee: Peking University People's Hospital, Beijing (CN)

( * ) Notice: Subject to any disclaimer, the term of this patent is extended or adjusted under 35 U.S.C. 154(b) by 194 days.

(21) Appl. No.: 12/523,085

(22) PCT Filed: Jan. 29, 2008

(86) PCT No.: PCT/CN2008/070211
§ 371 (c)(1),
(2), (4) Date: Jul. 14, 2009

(87) PCT Pub. No.: WO2008/095438
PCT Pub. Date: Aug. 14, 2008

(65) Prior Publication Data
US 2010/0055674 A1    Mar. 4, 2010

(30) Foreign Application Priority Data
Feb. 2, 2007    (CN) .......................... 2007 1 0003228

(51) Int. Cl.
*C12N 5/10*    (2006.01)
*C07N 7/06*    (2006.01)

(52) U.S. Cl. ...................................... 435/370; 435/235.1
(58) Field of Classification Search .................. None
See application file for complete search history.

(56) References Cited

FOREIGN PATENT DOCUMENTS
CN    101008004 A    8/2007
(Continued)

OTHER PUBLICATIONS
Huang et al. Cancer Research 2003, vol. 63, pp. 3775-3782.*
(Continued)

*Primary Examiner* — Bao Li
(74) *Attorney, Agent, or Firm* — Osha • Liang LLP

(57) ABSTRACT

The use of the liver cell line QSG-7701 for HBV infection includes the following steps: directly infecting QSG-7701 cells with purified HBV particles and facilitating the infection by DMSO and/or PEG treatment. The easily available QSG-7701 liver cell line may not require pre-differentiation induction and is naturally susceptible for HBV infection. This cell line provides near normal physiological conditions for HBV infection, especially the infection conditions that are characterized with Chinese origin. This cell line is suitable for investigating the life cycle of HBV. Therefore, this cell line is useful for the investigation of viral infection processes and for the development of drugs that specifically target these processes.

10 Claims, 3 Drawing Sheets

FOREIGN PATENT DOCUMENTS

WO    03-011209 A2    2/2003

OTHER PUBLICATIONS

Notification of First Office Action dated Nov. 23, 2008, from the State Intellectual Property Office of People's Republic of China, in related Chinese Patent Application No. 2007100032286, with English translation (13 pages).

Olive, Denise S., et al., "Cell culture and animal models for human viral hepatitis"; Hepatology Research 28 (2004), Elsevier.com/sciencedirect.com; pp. 61-67.

Partial English translation of the Response to the First Office Action filed Dec. 21, 2008, with the State Intellectual Property Office of People's Republic of China in related Chinese Patent Application No. 2007100032286 (2 pages).

Notice of Granting Patent Right for Invention issued Mar. 27, 2009, by the State Intellectual Property Office of People's Republic of China in related Chinese Patent Application No. 2007100032286, with English translation (2 pages).

International Search Report issued in PCT/CN2008/070211, mailed on May 8, 2008, with translation, 8 pages.

X. B. Pan, et. al., "Liver-derived cell lines QSG-7701 and HepG2 support different BV replication patterns"; Arch Virol (2007) 152: 1159-1173, Feb. 19, 2007.

Xiaoben Pan, et. al., "Comparisons of the characteristics and mechanisms of HBV replication in GSG-7701 and HepG2 cell line"; Chinese Journal of Hepatology (ISSN: 1007-3418), vol. 15, No. 2, pp. 83-87; Feb. 20, 2007 with English Abstract.

Xiaoben Pan, et. al., "QSG-7701 and HepG2: supporting different HBV replication pattern and different gene expression", Journal of Gastroenterology and Hepatology (2006), ISSN: 0815-9319, vol. 21, No. Suppl. 2, #A210; Dec. 31, 2006 (SEE: Methods and Conclusion).

Nir Paran, et. al., "HBV infection of cell culture: evidence for multivalent and cooperative attachment"; The EMBO Journal, vol. 20, No. 16; pp. 4443-4453; Dec. 31, 2001 (SEE:: abstract and discussion).

Christoph Seeger, et. al., "Hepatitis B Virus Biology"; Microbiology and Molecular Biology Reviews, vol. 64, No. 1, (Mar. 2000); pp. 51-68.

Chandan Guha, MD., PhD., et. al., "Cell Culture and Animal Models of Viral Hepatitis. Part I: Hepatitis B"; Lab Animal, vol. 33, No. 7; Jul./Aug. 2004; pp. 37-46.

Philippe Gripon, et. al., "Infection of a human hepatoma cell line by hepatitis B virus"; PNAS, vol. 99, No. 24 (Nov. 26, 2002); pp. 15655-15660.

\* cited by examiner

UTILIZING LIVER CELL LINE QSG-7701 TO BE INFECTED WITH HEPATITIS B VIRUS

CROSS REFERENCE TO RELATED APPLICATIONS

This is a national stage application of PCT/CN2008/070211, filed on Jan. 29, 2008, which claims priority to Chinese Application No. CN 200710003228.6, filed on Feb. 2, 2007.

FIELD OF THE INVENTION

The present invention relates to a cell line. In particular, it relates to the use of the cell line for hepatitis B virus infection.

BACKGROUND OF THE INVENTION

It has been over 40 years since the discovery of the "Australia antigen" in hepatitis B virus (HBV) from hemophiliac patients in 1965 by Blumberg. However, a thorough understanding of the life cycle of HBV has remained elusive so far, and there is no powerful drug for the treatment of chronic hepatitis B. The life cycle of HBV is pretty complex. The basic steps involves coupling of virus outer coat membrane with specific receptor(s) on the cell surface, entry of the virus into the cell through fusion of the viral membrane with cell membrane or phagocytosis, disassembly of the viral outer capsid in inclusion bodies, nuclear entry of core protein together with HBV DNA, which is repaired into cccDNA, and then transcription of various viral mRNAs and translation of the viral mRNAs into viral proteins for the assembly and secretion of viral particles (see Seeger C, Mason W S. Hepatitis B virus biology. *Microbiol. Mol. Biol. Rev.* 2000; 64:51-68). The detailed studies of HBV life cycle depends on a good HBV infection model system. Several cell lines, e.g., HepG2 and Huh-7, have been established that can support HBV replication after transfection with HBV DNA plasmids. However, transfection using HBV plasmids introduces the HBV DNA directly into these cells and does not involve the early steps of the HBV life cycle, such as virus interactions with specific cell membrane receptors, virus uncoating, and transport of the HBV DNA into the nucleus. Thus, these cell lines have limited use in the studies of the HBV life cycle. So far, only a few cells are known that can support HBV infection and replication. These cells include primary human liver cells (including embryonic liver cells), primary liver cells from tree shrew, and the recently established HepRG cells. Due to scarcity of the available sources, stringent requirements for isolation and culture conditions, and short survival time once isolated (generally less than 1 month), human primary liver cells and tree shrew primary liver cells are not suitable for scientific studies that require long-term investigation or large-scale cell culture (Guha C, Mohan S, Roy-Chowdhury N, et al. Cell culture and animal models of viral hepatitis, Part I: Hepatitis B. *Lab. Anim.* (NY) 2004; 33:37-46). HepRG cell line was established in 2002. This cell line is a liver progenitor cell line, which can be infected by HBV after pre-differentiation induction using DMSO. This cell line is not commercially available, but is only used in the lab where it was initially established. HepRG cells require pre-differentiation induction before they can be used in HBV infection studies. Stability and reproducibility of this model, however, are yet to be verified (see Gripon P, Rumin S, Urban S, et al. Infection of a human hepatoma cell line by the hepatitis B virus. *Proc. Nat. Acad. Sci. USA.* 2002; 99:1565-15660). Therefore, there is no reproducible cell line that can be used for the study of the complete HBV infection cycle. This lack of a suitable model has greatly impeded in-depth studies of various steps in the life cycle of HBV, especially the studies of the viral specific cellular receptor and the HBV DNA nuclear entry mechanism in the early stages of the HBV life cycle. The lack of a suitable cell line for HBV infection has also hindered the efforts to screen for and develop novel anti-HBV drugs. Therefore, identification of cell lines that are naturally susceptible to HBV infection remains important for the advancement of HBV research and for the development of therapeutics for chronic hepatitis.

DESCRIPTION OF THE INVENTION

The main objective of the present invention is to provide cell lines that are naturally susceptible to HBV infection.

Another objective of the present invention is to provide methods that may be employed to infect the described cell lines with HBV.

The above described objectives in the present invention are implemented with the following technical procedures.

The inventors of the present invention unexpectedly discover that the cell line QST-7701 may be susceptible to HBV infection and replication.

The liver cell line QSG-7701 was established in 1977, which was isolated from the tissue located 6 cm away from a tumor of a 35 year old female patient having the hepatocellular carcinoma. This cell line has an abnormal mitosis index of 6.2-14.3%. The chromosome of the cell line is subtriploid karyotype (mode 57). These cells express albumin. A small portion of QSG-7701 cells express alpha-fetoprotein. This cell line is considered to be precancerous hepatic cell line (see Dehou Zhu and Jinbing Wang, "Comparative study of hepatic cell line QSG-7701 and hepatoma cell line from human liver cancer," *Cancer Prevention and Treatment Research,* 1979: 7-9. In Chinese). This cell line is commercially available and can be purchased from suppliers, such as Shanghai Institute of Cell Biology, Chinese Academy of Science (Shanghai).

HBV infection of QSG-7701 liver cell line comprises the following step: directly infecting cultured QSG-7701 cells using purified HBV virus particles. A preferred procedure is: treating the cultured QSG-7701 cells with 1-2% DMSO, and then the cells may be infected with purified HBV virus particles and, simultaneously, add 2-4% PEG as infection adjuvant. A more preferred procedure is to infect the cultured QSG-7701 cells with purified HBV virus particles and, simultaneously, add 1-2% DMSO and 2-4% PEG as infection adjuvant.

QSG-7701 cell line has been used for about 30 years since its establishment. This cell line is stable and commercially available and, thus, can be obtained easily. In addition, this cell line may be used to overcome some disadvantages associated with using primary liver cell lines (e.g., human primary liver cell, embryo liver cell, and primary tree shrew liver cell line), such as difficulty to obtain and shorter in vitro life-span. Furthermore, HepRG cell line has not been commercialized. Therefore, it may be difficult to obtain HepRG cells because they may only be used by certain individual laboratories.

Different from HepRG cells in that cells become susceptible to HBV infection after pre-differentiation induction, QSG-7701 cells can be naturally infected by purified HBV. To a large extent, QSG-7701 cell line closely mimics the in vivo process by which HBV infects liver cell. Therefore, QSG-7701 cell line may be a suitable tool to study the life cycle of HBV. In particular, this cell line may be suitable for studying viral infection and for identifying relevant targets in the infection processes for the development of anti-viral drugs. For example, this cell line may be used to study the specific cell membrane receptors that interact with HBV, and the dynamics of nuclear translocation of the viral core particles carrying HBV DNA. Based on the data obtained from these studies, drugs may be developed, for example, to inhibit the binding of HBV to specific cell membrane receptors, to abolish disassembly of the core particles, and/or to inhibit nuclear translocation of HBV DNA.

The widely used liver (cancer) cell lines, such as HepG2 and Huh7, are derived from the tissues of Caucasian origin. In contrast, QSG-7701 cell line is derived from a Chinese female liver cancer patient. This cell line is derived from a surgically removed tissue around a tumor of this patient. In addition, QSG-7701 cell line has been identified as precancerous hepatic cells. Because this cell line was isolated from a Chinese, and is close to normal liver cells, this cell line, therefore, represents a suitable tool to study HBV replication in liver cells, specifically those of Chinese origin.

EXAMPLES

Figure 1A:
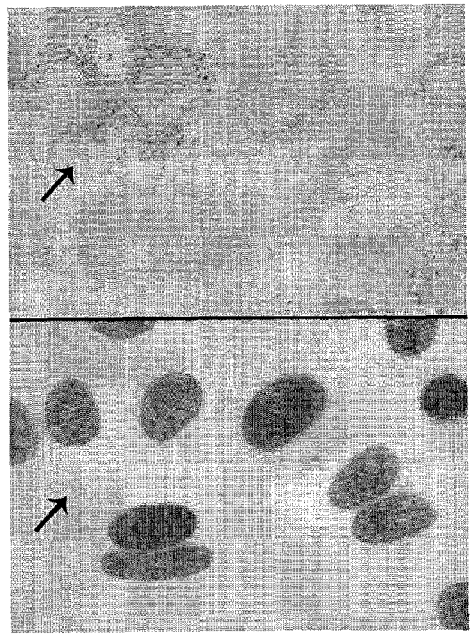
FIGS. 1A and 1C show the in vivo distribution of the core proteins in HepG2 cells 2-days after HBV infection. The core proteins (red) and the nuclei (blue) are indicated. The core proteins are mainly distributed in the cytoplasm after infection and HBV DNA may not be transported into the nucleus.
Figure 1B:
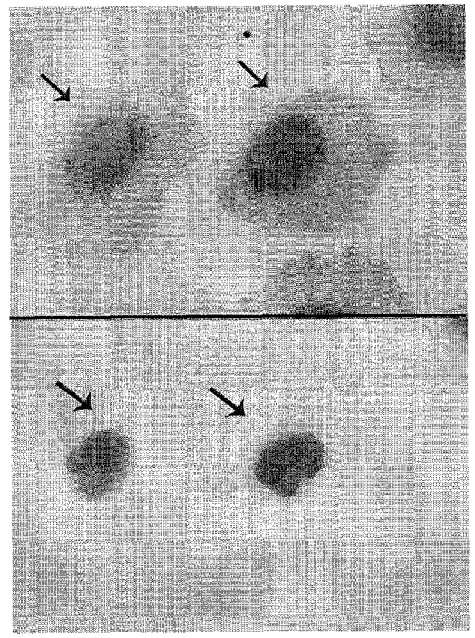
FIGS. 1B and 1D show the in vivo distribution of the core proteins in QSG-7701 cells 2-days after HBV infection. The core proteins (red) and the nuclei (blue) are indicated. The core proteins are mainly distributed in the nucleus and the peripheral regions of the nucleus.
Figure 1C:
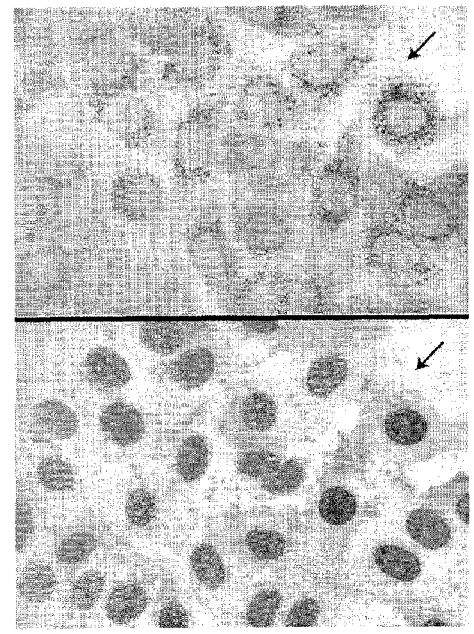
Figure 1D:
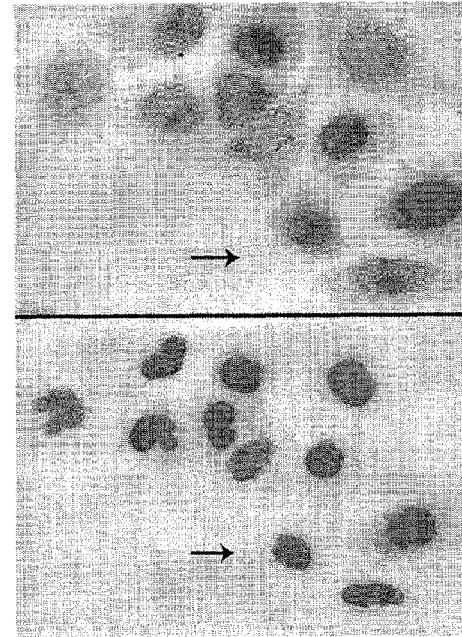

The following embodiments and figures are used to further illustrate the present invention.

HepG2 cell line is a classic liver cancer cell line, which supports HBV replication but may not be infected by HBV. To compare with this cell line, HBV-positive serum may be used to infect both HepG2 and QSG-7701 cells. The following examples describe the experimental procedures used for the viral infection.

Example 1

(1) Cell culture and infection: HBV-positive serum may be obtained from certain clinically tested samples. HBV may be concentrated up to $2\times10^{10}$ copies/ml using density gradient ultracentrifugation purification. HepG2 and QSG-7701 cell lines (purchased from Shanghai Institute of Cell Biology, Chinese Academy of Sciences, Shanghai, China) may be thawed, and cultured in 6-well plates containing 10% FBS (Hyclone, USA) DMEM culture medium (Sigma, USA). Infect the cells when they have grown to about 80% confluence. Replace the growth media with 2 ml of serum-free DMEM. Add 0.5 ml of HBV-positive serum (total amount of virus may be $1\times10^{10}$ copies/well). Cells may be incubated at 37° C. for 16 h. After incubation, cells may be washed 2 times with PBS followed by incubation for 2 min in the acid elution buffer (50 mM glycine, 150 mM NaCl, and add 1 M HCl to adjust to pH 2.2). Cells may then be washed 3 times with PBS to remove as many viruses as possible. Add 5% FBS DMEM culture medium and change to fresh culture media the next day. The supernatants may be centrifuged and stored at −20° C. for further testing.

(2) Detection of the HBcAg distribution using immunofluorescence cytochemistry: because a large amount of filamentous or spherical HBsAg particles may be present in the HBV-positive serum and only the intact Dane's viral particles contain core particles, HBcAg may be tagged to track the movement of viral particles. To detect cell entry and cellular distribution of HBcAg, SABC immunofluorescence cytochemistry staining technique may be used. The detection method may be as follows: after HepG2 and QSG-7701 cell lines are infected with HBV, they may be fixed in 4% paraformaldehyde overnight at 4° C., and then washed with 0.2% Trinton-PBS for 10 min. Add the primary anti-HBcAg antibody (1:100 dilutions, rabbit source, Signet, USA) overnight at 4° C., the secondary antibody may be the biotin-labeled goat anti-rabbit IgG (1:100), and then incubated at ambient temperature for 1 hour. Add streptavidin-labeled Cy3 (red fluorescence; Bioshide Biotechnology Co., China). Add immunofluorescent dye, DAPI (blue fluorescence; Vector, USA), for nuclear DNA staining. The slides may then be mounted. Digital images may be taken under a fluorescent microscope (Olympus, Japan) (FIG. 1). FIG. 1 is a black and white photo converted from a color photo taken in a test.

(3) Detection of viral replication intermediates: the viral replication intermediates may be detected using Southern blot analysis. Three days after infection, cells ($2\times10^6$) may be lysed in lysis buffer (50 mM Tris/HCl, pH 7.4, 1 mM EDTA, and 1% NP40). DNA may be extracted using the phenol/chloroform method. The Southern blot membranes may be exposed to X-ray film (Kodak, USA) for 30 min. The whole genomic probe of HBV may be prepared using digoxin labeling PCR kit (Roche, USA). The results are shown in FIG. 2.

Figure 3A:
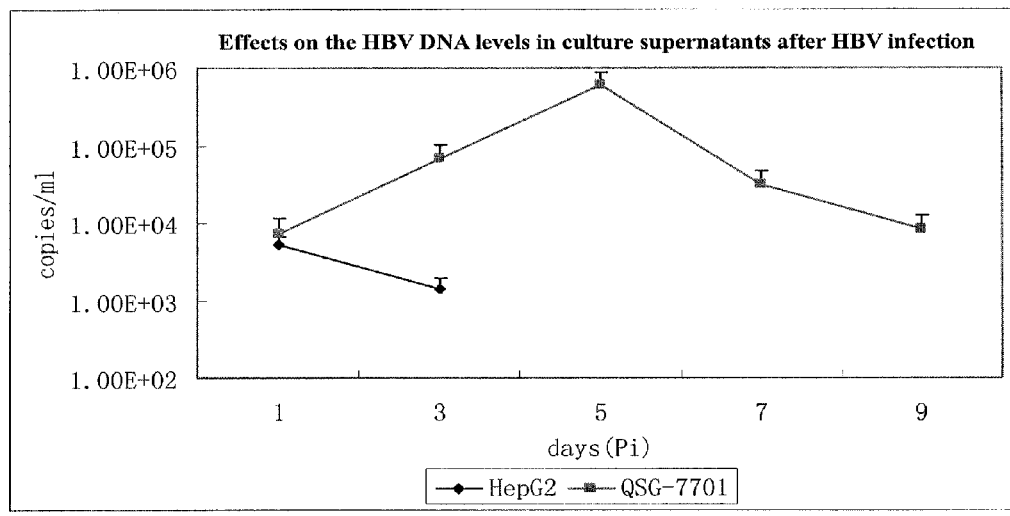
FIG. 3A shows the changes of HBV DNA levels in culture supernatant over time after infection.
Figure 3B:
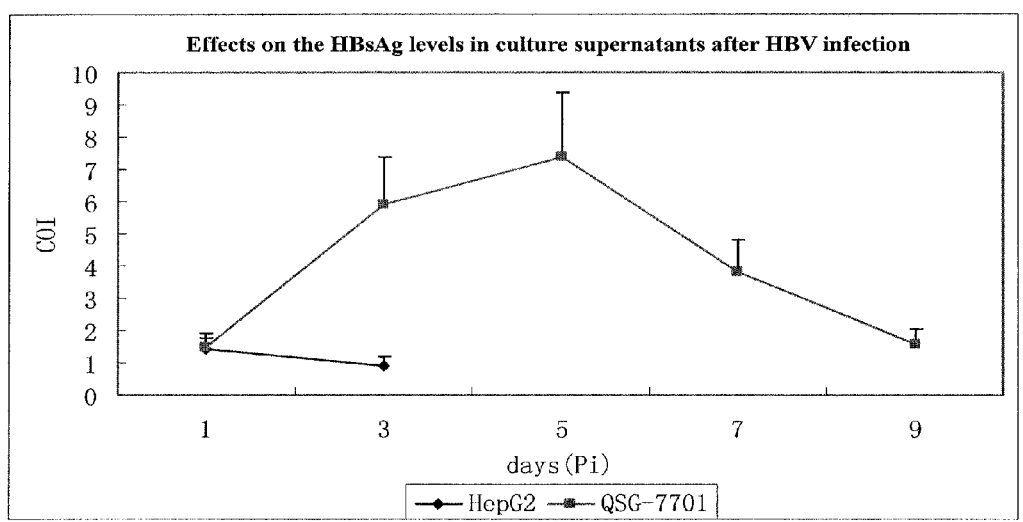
FIG. 3B shows the changes of HBsAg levels in culture supernatant over time after infection.

(4) Detection of HBsAg and HBV DNA in culture supernatants: the amount of HBsAg in the cell culture supernatant may be quantified using an electrochemical illumination detection kit (Roche, USA) and an automatic immunoassays analyzer (Roche, Elecsys 2010). The HBsAg standards may be provided by the kit. HBV DNA may be detected using a real time PCR detection kit (Shenzhen Piji Biotechnology Company, China) and a LightCycler real time quantitative PCR cycler (Roche). The PCR standards may be provided by the kit. Real time PCR may be performed according to the manual provided by the kit. This process may be repeated 5 times. FIGS. 3A and 3B show the results with statistical analysis.

FIG. 1 shows that some HepG2 cells infected with HBV (2 day after infection) have the core proteins distributed mainly in the cytoplasm but not in the nucleus. (As shown in FIGS. 1A and 1C, the arrows in the top panels indicate the black spotty signals from the core proteins. The arrows in the bottom panels indicate the black signals from the nucleus. 400× amplification) The data show that the core proteins may not enter the nucleus in HepG2 cells. In contrast, 2 days after HBV infection, there are strong core protein signals within the nucleus as well as the peripheral areas around the nucleus membrane in QSG-7701 cells. This observation suggests that there may be little barrier for the core proteins that carry HBV DNA, to enter the nucleus. (As shown in FIGS. 1B and 1D, the arrows in the top panels indicate the black spotty signals from the core proteins. The arrows in the bottom panels indicate the black signals from the nucleus. 400× amplification).

Figure 2:
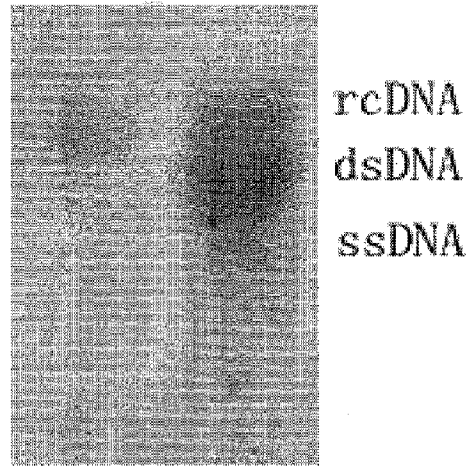
FIG. 2 shows the detection of HBV replication intermediates 3 days after HBV infection.

FIG. 2 shows the detection of HBV replication intermediates in cells 3 days after HBV infection. Only weak rcDNA signals may be detected in HepG2 cells without other replication intermediates. In contrast, after HBV infection, both dsDNA and ssDNA replication intermediate are detected in QSG-7701 cells.

FIG. 3A shows the changes of HBV DNA levels in the supernatants after HBV infection. FIG. 3B shows the changes of HBsAg levels in the supernatants after HBV infection. On the first and the third day post HepG2 infection, only trace amount of HBV DNA and HBsAg may be detected, and they become undetectable after the third day. This may be caused by the detachment of viruses from the cell surface and in the culture supernatant to be subsequently washed away. In contrast, the HBV DNA and HBsAg levels increase in the supernatants of QSG-7701 cells after HBV infection. In particular, the HBV DNA and HBsAg levels reach the maximum on the fifth day after infection, but gradually decrease thereafter. The HBV DNA and HBsAg levels remain detectable for about 9 days. It is possible that the cellular innate immunity inhibits the HBV replication.

The observation that the HBV-infected HepG2 cells do not have the viral replication intermediates indicates that HepG2 cells may not support HBV infection. This possibility is supported by other observations (see Paran N, Geiger B, Shaul Y., HBV infection of cell culture: evidence for multivalent and cooperative attachment. *EMBO J.* 2001; 20:4443-4453). In contrast, the observation that the core proteins are accumulated inside the nucleus of QSG-7701 cells infected with HBV indicates that QSG-7701 cells may support both the cell entry of HBV and the nuclear translocation of the core proteins carrying HBV DNA. The production of viral replication intermediates, and HBsAg and HBV DNA in the culture supernatants further support the idea that QSG-7701 cells can be successfully infected by HBV and that the cell line supports HBV replication.

Example 2

It may be performed basically according to the same procedure described in example 1, except that 1-2% DMSO is added to facilitate the viral infection.

Example 3

It may be performed basically according to the same procedure described in example 1, except that 2-4% PEG is added to facilitate the viral infection.

Example 4

It may be performed basically according to the same procedure described in example 1, except that both 1-2% DMSO and 2-4% PEG to facilitate the viral infection.

DMSO and PEG treatment may increase the number of viral particles attached to the cell surface, thus, facilitating HBV infection by enhancing the cellular intake of HBV particles. (see Glebe D, Berting, A, Broehl S, et al. Gerlich W H, and Schaefer S., Optimized conditions for the production of the hepatitis B virus from cell culture. *Intervirology,* 2001; 44(6):370-378). In addition, DMSO treatment may increase the levels of HBV DNA replication and viral protein expression. The mechanisms underlying these effects remain unclear.

These results show that, by simultaneously adding 1-2% DMSO and/or 2-4% PEG at viral infection, may further increase the stability of the model system as well as the viral replication levels.

The above embodiments are described only for the purpose of illustrating the present invention. Therefore, none of these embodiments should be regarded as limiting to the present invention. Those skilled in the art having an understanding of the essence of the present invention can modify or alter certain embodiments disclosed above. However, all such modifications are within the scope of the present invention.

What is claimed is:

1. An isolated liver cell line of QSG-7701 infected with purified HBV particles rather than a plasmid vector encoding a HBV DNA sequence.

2. The isolated liver cell line of QSG-7701 infected with HBV according to claim 1, wherein QSG-7701 cell line is directly infected with purified HBV particles.

3. The isolated liver cell line of QSG-7701 infected with HBV according to claim 1, wherein QSG-7701 cell line is treated with 1-2% DMSO, and then infected with purified HBV virus particles.

4. The isolated liver cell line of QSG-7701 infected with HBV according to claim 1, wherein QSG-7701 cell line is treated with 2-4% PEG to facilitate the infection.

5. The isolated liver cell line of QSG-7701 infected with HBV according to claim 1, wherein QSG-7701 cell line is treated with 1-2% DMSO and 2-4% PEG to facilitate the infection.

6. A method for studying HBV infection, comprising infecting QSG-7701 cells with purified HBV particles rather than a plasmid vector encoding a HBV DNA genome.

7. The method according to claim 6, wherein the QSG-7701 cells are directly infected with purified HBV particles.

8. The method according to claim 6, wherein the QSG-7701 cells are treated with 1-2% DMSO and then infected with purified HBV particles.

9. The method according to claim 6, wherein the QSG-7701 cells are treated with 2-4% PEG to facilitate the infection.

10. The method according to claim 6, wherein the QSG-7701 cells are treated with 1-2% DMSO and 2-4% PEG to facilitate the infection.

* * * * *